United States Patent [19]

Motley et al.

[11] Patent Number: 5,516,511

[45] Date of Patent: May 14, 1996

[54] ANTIPERSPIRANT GEL COMPOSITIONS COMPRISING CHELATORS

[75] Inventors: Curtis B. Motley; Barton J. Bradbury, both of West Chester, Ohio

[73] Assignee: The Procter & Gamble Company, Cincinnati, Ohio

[21] Appl. No.: 239,081

[22] Filed: May 6, 1994

[51] Int. Cl.$^6$ ............................. A61K 7/32; A61K 7/34
[52] U.S. Cl. ............................................ 424/65; 424/66
[58] Field of Search ..................................... 424/65, 66

[56] References Cited

U.S. PATENT DOCUMENTS

| | | | |
|---|---|---|---|
| 3,499,963 | 3/1970 | Rubino | 424/157 |
| 3,553,316 | 1/1971 | Rubino | 424/66 |
| 3,734,940 | 5/1973 | Rubino | 260/448 B |
| 5,232,689 | 8/1993 | Katsoulis et al. | 424/66 |
| 5,250,291 | 10/1993 | Park et al. | 424/66 |
| 5,254,332 | 10/1993 | Grezcyn et al. | 424/66 |

FOREIGN PATENT DOCUMENTS

| | | | |
|---|---|---|---|
| 0253552 | 1/1988 | European Pat. Off. | C01B 13/18 |
| 0266199 | 5/1988 | European Pat. Off. | C11D 1/72 |
| 0381165 | 8/1993 | European Pat. Off. | A61K 7/32 |
| 2371918 | 6/1978 | France | A61K 7/32 |
| 2689010 | 3/1992 | France | A61K 7/32 |
| 1-207223 | 8/1989 | Japan | A61K 7/02 |
| 845670 | 8/1960 | United Kingdom . | |
| 2076286A | 12/1981 | United Kingdom | A61K 33/40 |
| WO93/23008 | 11/1993 | WIPO | A61K 7/32 |
| WO94/24997 | 11/1994 | WIPO | A61K 7/32 |

OTHER PUBLICATIONS

Lange, N. A., "Analytical Chemistry, *Lange's Handbook of Chemistry*", (Ed. J. A. Dean), pp. 5–49–5–68, (1970).

*Primary Examiner*—Shelley A. Dodson
*Attorney, Agent, or Firm*—John M. Howell; Milton B. Graff, IV; Jacobus C. Rasser

[57] ABSTRACT

The subject invention relates to antiperspirant gel compositions comprising chelators. The subject invention also relates to a process for the manufacture of antiperspirant gel compositions comprising the steps of:

(a) pre-mixing a chelator with an antiperspirant active in a substantially water free environment; and (b) adding a gelling agent and a liquid base material to the product of step (a) in a substantially water free environment.

14 Claims, No Drawings

ANTIPERSPIRANT GEL COMPOSITIONS COMPRISING CHELATORS

FIELD OF THE INVENTION

The subject invention relates to antiperspirant gel compositions useful in preventing perspiration and body odors. Specifically, the subject invention relates to low-aqueous antiperspirant compositions in the form of a gel stick. The subject invention further relates to a process for the manufacture of the subject compositions.

BACKGROUND OF THE INVENTION

Personal hygiene habits typically include a means for reducing human body odor. These habits include routine bathing or washing of the body, particularly the axilla, and treating the axilla with compositions to retard odor formation, such as antiperspirant or deodorant compositions.

Antiperspirants generally include an astringent material in a suitable carrier. Astringent materials typically used in antiperspirants are metal salts, particularly aluminum and zirconium metal complexes. Exemplary metal salts are disclosed in Plechner, *Antiperspirants and Deodorants*, 2 Cosmetics, Science and Technology, Balsam and Sagafin, 374–400, 1972; incorporated herein by reference.

Antiperspirant compositions can be formulated in a variety of ways, each dependent on the particular ingredients involved. Such formulations include lotions, solid sticks, and creams. Solid stick formulations include gel sticks, which contain a liquid material and gelling agents.

One significant disadvantage of typical antiperspirant gel stick compositions is a tendency of the gelling agent to interact with acidic components present in antiperspirant actives or cationic species from other ingredient raw materials. This interaction between the gelling agent and the antiperspirant active can result in discoloration, odor, reduced efficacy of the actives, poor gel formation, and lower gel stability over time of any gel which is formed. The interaction may also cause processing difficulties at the temperatures and holding times typically encountered during manufacture. Antiperspirant gel stick compositions may have additional disadvantages such as a wet, cold and sticky feel on the skin, skin irritation, and shrinkage and containment problems due to high volatility.

It is an object of the subject invention to provide low-aqueous antiperspirant gel compositions with greater gel stability during manufacture, increased efficacy of the active as compared to current antiperspirant gel formulations, and reduced discoloration and odor.

It is also an object of the subject invention to provide low-aqueous antiperspirant gel stick compositions with greater gel stability during manufacture, increased efficacy of the active as compared to current antiperspirant gel formulations, and reduced discoloration and odor.

It is a further object of the subject invention to provide a process for the manufacture of low-aqueous antiperspirant gel compositions wherein the interaction between the active and gelling agent is reduced such that superior gel formation and greater gel stability can be achieved during manufacture, as well as reduced discoloration and odor.

SUMMARY OF THE INVENTION

The subject invention involves low-aqueous antiperspirant gel compositions comprising:

(a) an antiperspirant active;

(b) a gelling agent;

(c) a chelator; and (d) a liquid base material.

The subject invention also involves a process for manufacturing the subject compositions comprising the steps of:

(a) pre-mixing a chelator with an active in a substantially water-free environment; and (b) adding a gelling agent to the product of step (a) in a substantially water-free environment.

DETAILED DESCRIPTION OF THE INVENTION

It has been unexpectedly found that pre-mixing a chelator with certain antiperspirant actives allows the subject compositions to be held molten for extended periods of processing time without significant loss of product integrity. While not limited to any particular mechanism of action, it is believed that the chelator complexes with the metals in the formulation, especially in the active. Consequently, the active is prevented from reacting with the primary gellant, a reaction believed to interfere with the gelling process causing the gel to discolor, soften, and/or gain odor when held molten for extended periods of time during manufacture.

As used herein, the term "stick" means a non free flowing solid with a hardness of at least 75 grams of force, more preferably at least 100 grams of force, more preferably still at least 150 grams of force, as measured by using a Steven's-LFRA Texture analyzer with a 2 mm×64 mm steel blunt tip rod probe at 2 mm/sec to a constant depth. The depth of measurement is typically 15 mm for samples of approximately 10 g. For samples of approximately 3 g, the depth is 10 mm. Three readings are taken per sample and averaged. The typical standard deviation is approximately 10 g.

As used herein, the term "low-aqueous gel composition" means a gel composition comprising less than 50% water, preferably less than 40%, more preferably less than 30% water, also preferably less than 5% water. Gel compositions which are substantially water free are most preferred.

As used herein, the term "substantially water free" means that the only water content in the formulation comes from the degrees of hydration associated with the raw materials used in the formulation. No water is intentionally added.

As used herein, the term "alkyl" means carbon-containing chains which may be straight, branched or cyclic; substituted or unsubstituted; saturated, monounsaturated (i.e., one double or triple bond in the carbon chain), or polyunsaturated (i.e., two or more double bonds in the carbon chain, two or more triple bonds in the carbon chain, one or more double and one or more triple bonds in the carbon chain). Unless otherwise indicated, preferred alkyl are as follows. Preferred alkyl are straight or branched chain, more preferably straight chain. Preferred alkyl are mono-, di-, or tri-substituted, more preferably monosubstituted or unsubstituted, most preferably unsubstituted. Preferred alkyl are $C_1$ to $C_{26}$, more preferably $C_6$ to $C_{22}$, more preferably still $C_{12}$ to $C_{18}$.

As used herein, "substituted", in reference to alkyl groups, means such groups that can be mono- or polysubstituted. Preferred substituents are selected from the group consisting of halogen, hydroxy, amino, nitro, carboxy, thio, aryl, alkyl, alkoxy, and aryloxy. More preferred substituents include alkyl, alkoxy and aryl. The most preferred substituent is aryl.

As used herein, the term "aryl" means aromatic rings which may be unsubstituted or substituted. Preferred aryl are phenyl or naphthyl, especially phenyl. Preferred aryl are mono-, di- or tri- substituted, or unsubstituted; more preferred aryl are monosubstituted or unsubstituted. Preferred aryl substitutents include alkyl, halo, amino, hydroxy, alkoxy, cyano, nitro and trifluoromethyl.

As used herein, the term "alkoxy" means O-alkyl.

As used herein, the term "aryloxy" means O-aryl.

Gelling Agent

As used herein, the term "gelling agent" means a primary gellant; a secondary gellant; both discussed hereinafter, or a mixture thereof. The primary gellant is selected from the group consisting of 12-hydroxystearic acid, esters of 12-hydroxystearic acid, amides of 12-hydroxystearic acid and mixtures thereof. The secondary gellant is selected from the group consisting of n-acyl amino acid derivatives. The level of the gelling agent within the composition is typically from about 1% to about 15%; preferably, from about 3% to about 12%; more preferably, from about 5% to about 10%. If a mixture is used, the primary gellant:secondary gellant ratio is typically between about 1:2 and about 20:1; preferably, from about 1:1 to about 10:1; more preferably, from about 2:1 to about 7:1; and even more preferably, from about 3:1 to about 5:1.

The subject gelling agent offers significant benefits when used in an antiperspirant gel formulation, especially in a stick. The stick made with the gelling agent of the present invention exhibits decreased residue upon application to the skin, increased hardness and better aesthetics. The mixture of primary and secondary gellants is preferred to a similar composition having either of the two gellants alone. The primary and secondary gellants are, in combination, more effective than either alone so that the overall level of gelling agent within the composition can be reduced while maintaining such desirable stick characteristics.

Primary Gellant

As used herein, the term "primary gellant" means a compound selected from the group consisting of 12-hydroxystearic acid, esters of 12-hydroxystearic acid, amides of 12-hydroxystearic acid and mixtures thereof. Thus, the primary gellant corresponds to the following formula:

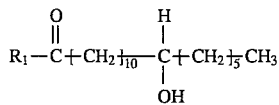

wherein:

(a) $R_1$ is $OR_2$ or $NR_2R_3$; and (b) $R_2$ and $R_3$ are, independently, hydrogen, alkyl, or aryl.
  At least one of $R_2$ or $R_3$ is preferably a hydrogen atom.

The primary gellant is preferably selected from the group consisting of 12-hydroxystearic acid, 12-hydroxystearic acid methyl ester, 12-hydroxystearic acid ethyl ester, 12-hydroxystearic acid stearyl ester, 12-hydroxystearic acid benzyl ester, 12-hydroxystearic acid amide, isopropyl amide of 12-hydroxystearic acid, butyl amide of 12-hydroxystearic acid, benzyl amide of 12-hydroxystearic acid, phenyl amide of 12-hydroxystearic acid, t-butyl amide of 12-hydroxystearic acid, cyclohexyl amide of 12-hydroxystearic acid, 1-adamantyl amide of 12-hydroxystearic acid, 2-adamantyl amide of 12-hydroxystearic acid, diisopropyl amide of 12-hydroxystearic acid, and mixtures thereof; even more preferably, 12-hydroxystearic acid, isopropyl amide of 12-hydroxystearic acid; and mixtures thereof.

Secondary Gellant

As used herein, the term "secondary gellant" means a compound selected from the group consisting of n-acyl amino acid derivatives, including n-acyl amino acid amides and n-acyl amino acid esters, preferably prepared from glutamic acid, alanine, lysine, glutamine, aspartic acid and mixtures thereof. Both d and l amino acids are effective in the subject invention. Natural amino acids (l isomers) are preferred. Preferred secondary gellants include n-acyl glutamic acid amides and n-acyl glutamic acid esters having the structure:

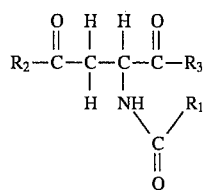

wherein:

(a) $R_1$ is alkyl, or aryl;

(b) $R_2$ and $R_3$ are, independently, alkyl ester, aryl ester, alkyl amide or aryl amide; $R_2$ and $R_3$ are preferably the same.

Preferably the n-acyl amino acid derivatives are selected from the group consisting of N-lauroylglutamic acid diethylamide, N-lauroylglutamic acid dibutylamide, N-lauroylglutamic acid dihexylamide, N-lauroylglutamic acid dioctylamide, N-lauroylglutamic acid didecylamide, N-lauroylglutamic acid didodecylamide, N-lauroylglutamic acid ditetradecylamide, N-lauroylglutamic acid dihexadecylamide, N-lauroylglutamic acid distearylamide, N-stearoylglutamic acid dibutylamide, N-stearoylglutamic acid dihexylamide, N-stearoylglutamic acid diheptylamide, N-stearoylglutamic acid dioctylamide, N-stearoylglutamic acid didecylamide, N-stearoylglutamic acid didodecylamide, N-stearoylglutamic acid ditetradecylamide, N-stearoylglutamic acid dihexadecylamide, N-stearoylglutamic acid distearylamide and mixtures thereof; more preferred, is n-lauroylglutamic acid dibutylamide, n-stearylglutamic acid dihexylamide; and mixtures thereof.

Liquid Base Material

A liquid base matrix of antiperspirant stick compositions of the subject invention is formed by combining the gelling agent with a liquid base material. As used herein, the term "liquid" refers to materials which are liquids at ambient conditions and the term "liquid base material" includes all liquids within the composition. It is important that the liquid base material be of a type, and used at a level sufficient to solubilize the gelling agent when heated, to permit substantially uniform mixing of the antiperspirant active into the heated solution at the mixing temperature, and form a stick when cooled to ambient temperature. The liquid base material must be compatible with the gelling agent so that the mixture of the two remains homogeneous and does not phase separate during manufacturing and so that the finished product remains homogeneous and does not phase separate at ambient conditions over the normal shelf-life which may be upwards of one year or more. Furthermore, the liquid base materials are typically selected to provide aesthetic benefits, such as emolliency, low tack or minimized visible residue, without significant interference with the effectiveness of the antiperspirant active component. The particular liquid base material should be safe for application to human skin.

The liquid base materials include emollients which have a solubility parameter from about 5 to about 11. It is preferable that, in aggregate, the average solubility parameter of the liquid base material be from about 6 to about 10. Hence, a mixture of emollients may be used as the liquid base material herein, each having a solubility parameter in the range of from about 5 to about 11, such that the average solubility parameter of the mixture is from about 6 to about 10. Solubility parameters are common to the art of antiperspirant stick formulation and the means to determine them are disclosed by C. D. Vaughan, "Solubility Effects in Product, Package, Penetration and Preservation" 103 Cosmetics and Toiletries 47–69, October, 1988; and C. D. Vaughan, "Using Solubility Parameters in Cosmetics Formulation", 36 *J Soc. Cosmetic Chemists* 319–333, Sept/Oct, 1985.

The liquid base material of the subject invention is preferably used at levels from about 10% to about 95% of the composition; and more preferably from about 45% to about 80%. The liquid base material preferably includes a volatile, non-polar, oil and a non-volatile, relatively polar co-solvent; each discussed more fully hereinafter. The term "non-volatile" as used herein refers to materials which exhibit a vapor pressure of no more than about 2.0 mm Hg at 25° C. at one atmosphere and/or to materials which have a boiling point at one atmosphere of at least about 300° C. The phrase "relatively polar" as used herein means more polar than another material in terms of solubility parameter; i.e., the higher the solubility parameter the more polar the liquid. The term "non-polar" typically means that the emollient has a solubility parameter below about 6.5.

Non-polar, Volatile Oil

The non-polar, volatile oil tends to impart highly desirable aesthetic properties to the gel stick. Consequently, the non-polar, volatile oils are preferably utilized at a fairly high level. Such non-polar, volatile oils are preferably used at levels from about 10% to about 70% of the composition; more preferably, from about 25% to about 60%; more preferably still from about 40% to about 60%.

Non-polar, volatile oils particularly useful in the present invention are selected from the group consisting of silicone oils; hydrocarbons; and mixtures thereof. Such non-polar, volatile oils are disclosed, for example, in Cosmetics, Science, and Technology, Vol. 1, 27–104 edited by Balsam and Sagafin, 1972. The non-polar, volatile oils useful in the present invention may be either saturated or unsaturated, have an aliphatic character and be straight or branched chained or contain alicyclic or aromatic rings. Examples of preferred non-polar, volatile hydrocarbons include isodecane (such as Permethyl-99A® which is available from Presperse Inc.) and the $C_7$–$C_8$ through $C_{12}$–$C_{15}$ isoparaffins (such as the Isopar® Series available from Exxon Chemicals).

Non-polar, volatile silicone oils are highly preferred as the non-polar, volatile oil in the liquid base material, since they endow the antiperspirant stick composition with highly desirable aesthetics. Non-polar, volatile liquid silicone oils are disclosed in U.S. Pat. No. 4,781,917 issued to Luebbe et al. on Nov. 1, 1988. Additionally, a description of various volatile silicones materials is found in Todd et al., "Volatile Silicone Fluids for Cosmetics", Cosmetics and Toiletries, 91:27–32 (1976). Particularly preferred volatile silicone oils are selected from the group consisting of cyclic volatile silicones corresponding to the formula:

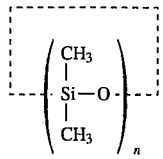

wherein n is from about 3 to about 7; and linear volatile silicones corresponding to the formula:

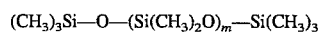

wherein m is from about 1 to about 7. Linear volatile silicones generally have a viscosity of less than about 5 centistokes at 25° C., whereas the cyclic silicones have viscosities of less than about 10 centistokes at 25° C. Highly preferred examples of volatile silicone oils include cyclomethicones of varying viscosities, e.g., Dow Corning 200®, Dow Corning 244®, Dow Corning 245®, Dow Corning 344®, and Dow Corning 345®, (commercially available from Dow Corning Corp.); SF-1204 and SF-1202 Silicone Fluids® (commercially available from G.E. Silicones), GE 7207® and 7158® (commercially available from General Electric Co.); and SWS-03314® (commercially available from SWS Silicones Corp.).

Relatively Polar, Non-volatile Co-solvent

The relatively polar co-solvent aids in the utilization of reduced processing temperatures by solubilizing at least one of the gellants and being soluble in the non-polar, volatile oil when subjected to reduced processing temperatures. The non-volatile co-solvent is "relatively polar" as compared to the non-polar, volatile oil discussed above. Therefore, the non-volatile co-solvent is more polar (i.e., has a higher solubility parameter) than at least one of the non-polar, volatile oils.

In addition to enabling reduced processing temperatures, the co-solvent enables the inclusion of greater amounts of the non-polar, volatile oil. This is advantageous because, as discussed above, the non-polar, volatile oil provides significant cosmetic benefits. The quantity of relatively polar, non-volatile co-solvent, however, is preferably kept to a minimum because it tends to adversely affect product cosmetics. Thus, the relatively polar, non-volatile co-solvent is preferably included at levels from about 5% to about 60%; more preferably from about 5% to about 25%; and most preferably from about 7% to about 20%.

Relatively polar, non-volatile liquids potentially useful as the co-solvent in the present invention are disclosed, for example, in Cosmetics, Science, and Technology, Vol. 1, 27–104 edited by Balsam and Sagarin, 1972; U.S. Pat. No. 4,202,879 issued to Shelton on May 13, 1980; and U.S. Pat. No. 4,816,261 issued to Luebbe et al. on Mar. 28, 1989. Relatively polar, non-volatile co-solvents useful in the present invention are preferably selected from the group consisting of silicone oils; hydrocarbon oils; fatty alcohols; fatty acids; esters of mono and dibasic carboxylic acids with mono and polyhydric alcohols; polyoxyethylenes; polyoxypropylenes; mixtures of polyoxyethylene and polyoxypropylene ethers of fatty alcohols; and mixtures thereof. The relatively polar, non-volatile co-solvents useful in the present invention may be either saturated or unsaturated, have an aliphatic character and be straight or branched chained or contain aliphatic or aromatic rings.

More preferably, the relatively polar, non-volatile liquid co-solvent are selected from the group consisting of fatty alcohols having from about 12–26 carbon atoms; fatty acids having from about 12–26 carbon atoms; esters of monobasic carboxylic acids and alcohols having from about 14–30 carbon atoms; esters of dibasic carboxylic acids and alcohols having from about 10–30 carbon atoms; esters of polyhydric alcohols and carboxylic acids having from about 5–26 carbon atoms; ethoxylated, propoxylated, and mixtures of ethoxylated and propoxylated ethers of fatty alcohols with from about 12–26 carbon atoms and a degree of ethoxylation and propoxylation of below about 50; and mixtures thereof.

More preferred are propoxylated ethers of $C_{14}$–$C_{18}$ fatty alcohols having a degree of propoxylation below about 50, esters of $C_2$–$C_8$ alcohols and $C_{12}$–$C_{26}$ carboxylic acids (e.g. ethyl myristate, isopropyl palmitate), esters of $C_{12}$–$C_{26}$ alcohols and benzoic acid (e.g. Finsolv TN® supplied by Finetex), diesters of $C_2$–$C_8$ alcohols and adipic, sebacic, and phthalic acids (e.g., diisopropyl sebacate, diisopropyl adipate, di-n-butyl phthalate), polyhydric alcohol esters of $C_6$–$C_{26}$ carboxylic acids (e.g., propylene glycol dicaprate/ dicaprylate, propylene glycol isostearate); and mixtures thereof.

Even more preferred are branched-chain aliphatic fatty alcohols having from about 12–26 carbon atoms. Even more preferred is isocetyl alcohol, octyldecanol, octyldodecanol and undecylpentadecanol; and most preferred is octyldodecanol. Such preferred aliphatic fatty alcohols are particularly useful in combination with the volatile liquid silicone oils discussed herein to adjust the average solubility of the liquid base material.

Non-polar, Non-volatile Emollients

In addition to the liquids discussed above, the liquid base material may optionally include non-volatile, non-polar emollients which tend to improve product cosmetics. Typical non-volatile, non-polar emollients are disclosed, for example, in Cosmetics, Science, and Technology, Vol. 1, 27–104 edited by Balsam and Sagarin, 1972; U.S. Pat. No. 4,202,879 issued to Shelton on May 13, 1980; and U.S. Pat. No. 4,816,261 issued to Luebbe et al. on Mar. 28, 1989. The non-volatile silicone oils useful in the subject invention are essentially non-volatile polysiloxanes, paraffinic hydrocarbon oils, and mixtures thereof. The polysiloxanes useful in the subject invention are selected from the group consisting of polyalkylsiloxanes, polyarylsiloxanes, polyalkylarylsiloxanes, poly-ethersiloxane copolymers, and mixtures thereof. Examples of these include polydimethyl siloxanes having viscosities of from about 5 to about 100,000 centistokes at 25° C.

Among the preferred non-volatile silicone emollients useful in the present compositions are the polydimethyl siloxanes having viscosities from about 2 to about 400 centistokes at 25° C. Such polyalkylsiloxanes include the Viscasil® series (sold by General Electric Company) and the Dow Corning 200® series (sold by Dow Corning Corp.). Polyalkylarylsiloxanes include polymethylphenyl siloxanes having viscosities of from about 15 to about 65 centistokes at 25° C. These are available, for example, as SF 1075® methyl-phenyl fluid (sold by General Electric Company) and 556 Cosmetic Grade Fluid® (sold by Dow Corning Corp.).

Useful polyethersiloxane copolymers include, for example, a polyoxyalkylene ether copolymer having a viscosity of about 1200 to 1500 centistokes at 25° C. Such a fluid is available as SF1066® organosilicone surfactant (sold by General Electric Company). Polysiloxane ethylene glycol ether copolymers are preferred copolymers for use in the present compositions.

Non-volatile paraffinic hydrocarbon oils useful in the present invention include mineral oils and certain branched-chain hydrocarbons. Examples of these fluids are disclosed in U.S. Pat. No. 5,019,375 issued to Tanner et al. on May 28, 1991. Preferred mineral oils have the following properties: viscosity from about 5 centistokes to about 70 centistokes at 40° C.; density between about 0.82 and 0.89 g/cm$^3$ at 25° C.; flash point between about 138° C. and about 216° C.; and carbon chain length between about 14 and about 40 carbon atoms. Preferred branched chain hydrocarbon oils have the following properties: density between about 0.79 and about 0.89 g/cm$^3$ at 20° C.; boiling point greater than about 250° C.; and flash point between about 110° C. and about 200° C.

Particularly preferred branched-chain hydrocarbons include Permethyl 103A®, which contains an average of about 24 carbon atoms; Permethyl 104A®, which contains an average of about 68 carbon atoms; Permethyl 102A®, which contains an average of about 20 carbon atoms; all of which may be purchased from Permethyl Corporation; and Ethylflo 364® which contains a mixture of 30 carbon atoms and 40 carbon atoms and may be purchased from Ethyl Corp.

Antiperspirant Active

The compositions of the subject invention also contain an astringent antiperspirant active. Antiperspirant actives useful in the subject invention are well known in the art. See e.g., "Antiperspirant and Deodorants", *Cosmetic Science and Technology Series,* K. Laden & C. Felger, eds., Vol. 7., pp. 42–56 (1988); incorporated herein by reference. These actives are used at levels from about 0.5% to about 60% of the composition, preferably from about 5% to about 35%, of the antiperspirant gel composition. This active may be incorporated in gel stick formulations either in solubilized or particulate form. These weight percentages are calculated on an anhydrous metal salt basis (exclusive of glycine, the salts of glycine, or other complexing agents). Such materials include, for example, many aluminum or zirconium astringent salts or complexes and are well known in the antiperspirant art.

Reduction in the amount of interaction between the antiperspirant active and the gelling agent results in better gel stick compositions. This interaction can be reduced by decreasing the surface area of the antiperspirant active; thereby reducing the interaction sites. Consequently, the antiperspirant active is preferably in particulate form wherein the surface area of the active is relatively low. The surface area of the antiperspirant active can be reduced by increasing the size and density of the active particles. Consequently, the particulate antiperspirant active preferably has a density which is preferably greater than about 0.7 g/cm$^3$ and an average particle size (as measured by a Coulter Multisizer 11® manufactured by Coulter Corporation, Haleah, Fla.) greater than about 10 microns; more preferably, greater than about 30 microns; and most preferably, greater than about 40 microns. Such preferred materials can be purchased from Westwood Chemical Company, Middletown, N.Y. under the trade name Westchlor ZR®. Suitable antiperspirant active is disclosed, for example in U.S. Pat. No. 4,147,766 which issued on Apr. 3, 1979 to Kozischek.

Any aluminum astringent antiperspirant salt or aluminum and/or zirconium astringent complex can be employed herein. Salts useful as astringent antiperspirant salts or as components of astringent complexes include aluminum halides, aluminum hydroxy-halides, zirconyl oxyhalides, zirconyl hydroxy-halides, and mixtures of these materials.

Aluminum salts of this type include aluminum chloride and the aluminum hydroxyhalides having the general formula $Al_2(OH)_xQ_y.XH_2O$ wherein:

(a) Q is chlorine, bromine or iodine;

(b) x is from about 2 to about 5, and x+y=about 6, and x and y do not need to be integers; and (c) X is from about 1 to about 6.

Aluminum salts of this type can be prepared in the manner described more fully in U.S. Pat. No. 3,887,692 issued to Gilman on Jun. 3, 1975, and U.S. Pat. No. 3,904,741 issued to Jones and Rubino on Sep. 9, 1975.

The zirconium compounds which are useful in the present invention include both the zirconium oxy salts and zirconium hydroxy salts, also referred to as the zirconyl salts and zirconyl hydroxy salts. These compounds may be represented by the following general empirical formula:

$$ZrO(OH)_{2-nz}B_z$$

wherein:

(a) z may vary from about 0.9 to about 2 and need not be an integer;

(b) n is the valence or B;

(c) 2-nz is greater than or equal to 0:

(d) B is selected from the group consisting of halides, nitrate, sulfamate, sulfate, and mixtures thereof.

Although only zirconium compounds are exemplified in this specification, other Group IVB metal compounds, including hafnium, can be used in the subject invention.

As with the basic aluminum compounds, the above formula is greatly simplified and is intended to represent and include compounds having coordinated and/or bound water in various quantities, as well as polymers, mixtures and complexes of the above. As will be seen from the above formula, the zirconium hydroxy salts actually represent a range of compounds having various amounts of the hydroxy group, varying from about 1.1 to only slightly greater than zero groups per molecule.

Several types of antiperspirant complexes utilizing the above antiperspirant salts are known in the art. For example, U.S. Pat. No. 3,792,068 issued to Luedders et al. on Feb. 12, 1974 discloses complexes of aluminum, zirconium and amino acids, such as glycine. Complexes such as those disclosed in the Luedders et al. patent and other similar complexes are commonly known as ZAG. ZAG complexes are chemically analyzable for the presence of aluminum, zirconium and chlorine. ZAG complexes useful herein are identified by the specification of both the molar ratio of aluminum to zirconium (hereinafter "Al:Zr" ratio) and the molar ratio of total metal to chlorine (hereinafter "Metal:Cl" ratio). ZAG complexes useful herein have an Al:Zr ratio of from about 1.67 to about 12.5 and a Metal:Cl ratio of from about 0.73 to about 1.93.

Preferred ZAG complexes are formed by (A) co-dissolving in water (1) one part $Al_2(OH)_{6-m}Q_m$, wherein Q is an anion selected from the group consisting of chloride, bromide and iodide, and m is a number from about 0.8 to about 2.0;

(2) x parts $ZrO(OH)_{2-a}Q_a.nH_2O$, where Q is chloride, bromide or iodide; where a is from about 1 to about 2; where n is from about 1 to about 8; and where x has a value of from about 0.16 to about 1.2;

(3) p parts neutral amino acid selected from the group consisting of glycine, dl-tryptophane, dl-b-phenyla-lanine, dl-valine, dl-methionine and b-alanine, and where p has a value of from about 0.06 to about 0.53;

(B) co-drying the resultant mixture to a friable solid; and (C) reducing the resultant dried inorganic-organic antiperspirant complex to particulate form.

A preferred aluminum compound for preparation of such ZAG type complexes is aluminum chlorhydroxide of the empirical formula $Al_2(OH)_5Cl.2H_2O$. Preferred zirconium compounds for preparation of such ZAG-type complexes are zirconyl hydroxychloride having the empirical formula $ZrO(OH)Cl.3H_2O$ and the zirconyl hydroxyhalides of the empirical formula $ZrO(OH)_{2-a}Cl_2.nH_2O$ wherein a is from about 1.5 to about 1.87, and n is from about 1 to about 7. The preferred amino acid for preparing such ZAG-type complexes is glycine of the formula $CH_2(NH_2)COOH$. Salts of such amino acids can also be employed in the antiperspirant complexes. See U.S. Pat. No. 4,017,599 issued to Rubino on Apr. 12, 1977.

A wide variety of other types of antiperspirant complexes are also known in the art. For example, U.S. Pat. No. 3,903,258 issued to Siegal on Sep. 2, 1975 discloses a zirconium aluminum complex prepared by reacting zirconyl chloride with aluminum hydroxide and aluminum chlorhydroxide. U.S. Pat. No. 3,979,510 issued to Rubino on Sep. 7, 1976 discloses an antiperspirant complex formed from certain aluminum compounds, certain zirconium compounds, and certain complex aluminum buffers. U.S. Pat. No. 3,981,896 issued to Pauling on Sep. 21, 1976 discloses an antiperspirant complex prepared from an aluminum polyol compound, a zirconium compound and an organic buffer. U.S. Pat. No. 3,970,748 issued to Mecca on Jul. 20, 1976 discloses an aluminum chlorhydroxy glycinate complex of the approximate general formula $(Al_2(OH)_4Cl)(H_2CNH_2COOH)$.

Of all the above types of antiperspirant actives, preferred compounds include the 5/6 basic aluminum salts of the empirical formula $Al_2(OH)_5Cl.2H_2O$; mixtures of $AlCl_3.6H_2O$ and $Al_2(OH)_5Cl.2H_2O$ with aluminum chloride to aluminum hydroxychloride weight ratios of up to about 0.5; ZAG type complexes wherein the zirconium salt is $ZrO(OH)Cl.3H_2O$, the aluminum salt is $Al_2(OH)_5Cl.2H_2O$ or the aforementioned mixtures of $AlCl_3.6H_2O$ and $Al_2(OH)_5Cl.2H_2O$ wherein the total metal to chloride molar ratio in the complex is less than about 1.25 and the Al:Zr molar ratio is about 3.3, and the amino acid is glycine; and ZAG-type complexes wherein the zirconium salt is $ZrO(OH)_{2-a}Cl_a.nH_2O$ wherein a is from about 1.5 to about 1.87 and n is from about 1 to about 7, the aluminum salt is $Al_2(OH)_5Cl.2H_2O$, and the amino acid is glycine.

Solubilized antiperspirant actives which may be utilized in the present invention are also well known in the art. These materials utilize monohydric or polyhydric alcohols or water to solublize the antiperspirant active before it is incorporated into the product. The levels of these polar solvents is less than 25%, and preferably less than 15% of the composition. Examples of such actives are taught, for example, in U.S. Pat. No. 4,137,306 issued to Rubino on Jan. 30, 1979; U.S. patent application Ser. No. 370,559, Smith and Ward, filed Jun. 23, 1989; and European Patent Application 0295070 which published Dec. 14, 1988.

Chelators

The compositions of the subject invention comprise a chelator that has been pre-mixed in the base liquid with the antiperspirant active to prevent reaction between the active and the primary gellant. As used herein, the term "chelator" means any compound capable of complexing with metal ions present in the subject actives or present in any other component of the formulation.

The level of chelator used depends on the chelator involved and the number of sites on the particular chelator that bind to the metal ions. Typically, the chelators of the subject compositions preferably comprise from about 0.01% to about 10% of the composition, more preferably from about 0.05% to about 5% of the composition, more preferably still from about 0.1% to about 2% of the composition, also preferably about 0.2% of the composition.

Preferred chelators useful in the subject invention include acetylacetone, ethylene diamine-N,N,N',N'-tetracetic acid (EDTA), nitrilotriacetic acid, oxalate, citric acid, 1,2-diaminocyclohexane-N,N,N'N'-tetracetic acid, 4,5-dihydroxybenzene-1,3-disulfonic acid, pyrocatechol-3,5-disulfonate, salicylic acid, 5-sulfosalicylic acid, xylenol orange, aurintricarboxylic acid, 2,2'-pyridyl ethylene diamine, glycine, 8-hydroxyquinoline-5-sulfonic acid, lactic acid, 1,10-phenanthroline, pyridine, pyridine-2,6-dicarboxylic acid, 8-quinolinol, succinic acid, tartaric acid, thioglycolic acid, 1,1,1-trifluoro-3,2'-thenolyacetone and triethylene tetramine.

More preferred chelators include acetylacetone, EDTA, nitrilotriacetic acid, oxalate, citric acid, 1,2-diaminocyclohexane-N,N,N'N'-tetracetic acid, 4,5-dihydroxybenzene-1,3-disulfonic acid, pyrocatechol-3,5-disulfonate, salicylic acid, 5-sulfosalicylic acid and xylenol orange. Even more preferred chelators include acetylacetone, EDTA, nitrilotriacetic acid and oxalate. The most preferred chelator is EDTA.

The subject chelators may be used in their salt form. Preferred salts of the subject chelators include mono and divalent cations and combinations thereof, to provide a total charge of 0 to about 4. More preferred salts are $Na^+$, $K^+$, $Li^+$ and $Mg^{++}$, and mixtures thereof, more preferably still $Na^+$ and $K^+$ and mixtures thereof. A particularly preferred chelator is disodium EDTA.

Optional Ingredients

Antiperspirant gel stick compositions of the subject invention may contain optional components which act as additional active or modify the physical characteristics of the composition or the components making up said compositions. Such components are well known in the art. A non-limiting group of these optional components include colorants, perfumes, thickeners, distributing agents, emulsifiers, bacteriostats, fungistats, and mixtures thereof. Optional components useful herein are described in the following references: U.S. Pat. No. 4,049,792 issued to Elsnau on Sep. 20, 1977; Canadian Patent 1,164,347 which issued to Beckmeyer et al. on Mar. 27, 1984; European Patent Application 117,070 which published on Aug. 29, 1984; and Geria, "Formulation of Stick Antiperspirants and Deodorants", *Cosmetics and Toiletries*, 99:55–60 (1984).

Emulsifiers are particularly useful in the subject invention. These emulsifiers include non-ionic surfactants useful for forming water-in-oil emulsions. The level of emulsifiers used in the subject invention is typically less than about 10% of the composition, preferably less than about 5%. Examples of these emulsifiers include polyoxyethylene ethers of fatty alcohols, and polyoxyethylene-polysiloxane copolymers. Such emulsifiers are disclosed by EPO Application 373,424 Raleigh et al., and U.S. Ser. No. 530,671, Cedeno et al., filed Jul. 2, 1991.

Thickeners are also useful in the subject invention. Their selection and the level they are used at should be so as not to significantly affect the aesthetics of the gel composition. Typical levels of thickeners are at levels of less than about 5%. Examples of said thickeners are disclosed in U.S. Pat. No. 4,985,238, Tanner et al., issued Jan. 15, 1991; herein incorporated by reference. These thickeners include wax-like materials such as beeswax, cerasin, hydrogenated castor oil, synthetic waxes such as Fisher Tropsch waxes, microcrystalline waxes, polyethylene waxes, and mixtures thereof.

Particulate and filler materials may also be included in the subject compositions. These materials are typically used at levels from about 0.5% to about 5% of the composition, preferably not more than 3%. Such materials are disclosed in U.S. Pat. No. 5,019,375, Tanner et al., issued May 28, 1991. Suitable filler materials include collodial silica (such as Cab-O-Sil®, sold by Cabot Corp.), clays (such as bentonite), hydrophobic (quaternized) clays, silica/alumina thickeners, silicate powders such as talc, alumina silicate, and magnesium silicate, modified corn starches, metallic stearates, and mixtures thereof. The use of such fillers as stabilizing agents in cosmetic sticks is disclosed in U.S. Pat. No. 4,126,679, Davy et al., issued Nov. 21, 1987, incorporated by reference. Examples of other particulate materials include particulate hydrophilic polymers such as cellulose ether polymers, modified starches, polyamides, and polypeptides.

A wash-off agent may be utilized to improve the ease with which the ingredients—particularly the gelling agent and the non-polar, non-volatile oils—may be washed off. The wash-off agent is highly preferably a non-liquid. The wash-off agent is typically in the antiperspirant stick composition in an amount from about 0.1% to about 10% of the composition.

Typical wash-off agents are non-liquids selected from the group consisting of polyoxyethylene ethers having the formula $R_1(OCH_2CH_2)_nOH$; polyoxyethylene esters having the formula $R_1CO(OCH_2CH_2)_nOH$; polyoxyethylene glyceryl esters having the formula $(R_1COO)CH_2CH(OH)CH_2(OCH_2CH_2)_nOH$ or having the formula $HOCH_2CH(OOCR_1)CH_2(OCH_2CH_2)_nOH$; and polyoxyethylene glyceryl diesters having the formula $R_1COOCH_2CH(OOCR_2)CH_2(OCH_2CH_2)_nOH$—preferably, the polyoxyethylene ethers—wherein: $R_1$ and $R_2$ are, independently, alkyl, alkenyl, or aromatic hydrocarbon which may be substituted or unsubstituted— preferably an alkyl radical—having from about 4 to about 22 carbon atoms; and n is from about 2 to about 80.

Preferred examples of such wash-off agents include: ceteth-2 through ceteth-30, steareth-2 through steareth-30, ceteareth-2 through ceteareth-30, PEG-2 stearate through PEG-30 stearate, PEG-12 isostearate, PEG-16 hydrogenated castor oil, PEG-40 hydrogenated castor oil, Unithox 480® and 425®, and PEG-20 glyceryl stearate; more preferably, ceteareth-20, steareth-21, PEG-20 stearate, Unithox 480® and 425®, and PEG-16 hydrogenated castor oil; more preferably still, ceteareth-20 and Unithox 480® and 425®; also preferably Unithox 480® and 425®.

METHODS OF MANUFACTURE

The chelator and antiperspirant active are premixed in a solvent of choice in a vessel equipped with a heat source at a temperature of about 200° F., for about 15 minutes to about one hour. The gelling agent and the liquid base material are combined separately in a vessel equipped with a heat source. The mixture is heated to about 200° F., with stirring, until the mixture forms a homogeneous, molten solution. The solution containing the antiperspirant active and chelator is mixed into the homogeneous, molten solution in the above vessel with stirring, maintaining the temperature at about 200° F. Optional components such as fragrances and colors may also be mixed into the homogeneous solution at this time. Preferably, the homogeneous, molten solution is allowed to cool to a mixing temperature; typically between about 135° F. and 145° F. Alternatively, the mixture may simply be heated to the mixing temperature until the mixture forms a homogeneous, molten solution. This alternative method, however, typically takes longer than simply overheating and then cooling. The mixture is allowed to cool until it begins thickening and then is poured into containers allowing them to cool to ambient temperature; the mixture is allowed to solidify into a gel.

METHODS FOR USE

The subject invention provides methods for preventing perspiration and malodor associated with human perspiration. These methods comprise applying to the skin of a human a safe and effective amount of the antiperspirant gel of the present invention. The term "a safe and effective amount" as used herein, is an amount which is effective in eliminating or substantially reducing malodor associated with human underarm perspiration while being safe for human use at a reasonable risk/benefit ratio. Typically, the safe and effective amount used is from about 0.1 gram per axilla to about 1.0 gram per axilla.

EXAMPLES

The following examples further describe and demonstrate embodiments within the scope of the present invention. These examples are solely for the purpose of illustration and are not to be construed as limitations of the present invention as many variations are possible without departing from the spirit or scope thereof.

The levels of the components in the examples below are expressed by percentages of total weight of the composition.

Example I

| COMPONENT | |
|---|---|
| Octyldodecanol | 14 |
| 12-Hydroxystearic acid | 7 |
| N-Lauroyl Glutamate Dibutylamide[1] | 2 |
| Unithox 480 ® | 1.25 |
| Unithox 425 ® | 0.5 |
| EDTA | 1 |
| Aluminum Zirconium Trichlorohydrex Gly ®[2] | 26 |
| Cyclomethicone D-5[3] | q.s. |

[1] Supplied by Starks Chemical Co
[2] Supplied by Westwood Chemical Co.
[3] Dow Corning 245 ® Fluid-cyclic polydimethylsiloxane Half the cyclomethicone D-5 is placed in a mix tank. Unithox 480, Unithox 425 and 12-hydroxystearic acid are added. The tank is heated until the temperature is approximately 200° F. The N-lauroyl glutamate dibutylamide is homogenized into all of the octyldodecanol and the resulting slurry added to the mix tank. The contents of the mix tank are heated until a clear solution is achieved. While the mix tank is heating, the active, EDTA and the other half of the cyclomethicone D-5 are added into a separate mix tank. The active and EDTA are slurried for 45 minutes and heated to about 200° F. The active/EDTA slurry is added to the first mix tank and heated with stirring to maintain a temperature of about 200° F. The product is circulated through a cooling heat exchanger to bring it down to between about 135° F. and about 145° F., so that it is thick enough to prevent active settling. The mixture is cooled further and solidified to form a gel.

Examples II through XXVI can be prepared using similar mixing techniques.

| | EXAMPLE NUMBER | | | | | | | |
|---|---|---|---|---|---|---|---|---|
| COMPONENT | II | III | IV | V | VI | VII | VIII | IX |
| N-Lauroyl-L-glutamic acid-di-n-butyl amide[1] | 4 | 5 | 1 | 3 | 2 | 2 | 2 | 1 |
| 12-hydroxystearic acid | 2 | 5 | 5 | 6 | 7 | 3 | 6 | 12 |
| Cyclomethicone D-5[2] | | q.s. | q.s. | q.s. | q.s. | q.s. | q.s. | q.s. |
| Polyphenylmethylsiloxane[3] | | | | 3 | | | 5 | |
| Light mineral oil[4] | q.s. | | | | | | | |
| Panalane-L-14E ®[5] | | 15 | 10 | 11 | | | | |
| Isopropyl Myristate | | 15 | 15 | 16 | | | 11 | |
| Isopropyl Alcohol | | | | | 18 | | | |
| Captex 200 ®[6] | | | | | | 15 | | |
| C$_{12}$-C$_{15}$ Alcohols Benzoate[7] | | | | | | | 8 | |
| PPG-3 Myristyl Ether | | | | | | | | 26 |
| Diisopropyl Sebacate[8] | 43 | | | | | | | |
| Aluminum Zirconium Trichlorhydrex Gly ®[9] | 25 | 20 | 20 | 20 | | 40 | 25 | |
| Aluminum Chlorohydrate[10] | | | | | 30 | | | 10 |
| EDTA | 0.2 | 0.1 | 0.5 | 1 | 5 | 10 | 7 | 0.01 |
| Talc | 3 | | | 2 | | | | 5 |

[1] GP-1 ® supplied by Ajinomoto, Inc.
[2] Dow Corning 245 ® Fluid-cyclic polydimethylsiloxane
[3] Dow Corning 556 ® Fluid
[4] Benol White Mineral Oil supplied by Witco Chemical Corp.
[5] polyisobutene supplied by Amoco Chemical Company
[6] propylene glycol dicaprate/dicaprylate supplied by Capital City Products
[7] Finsolv TN ® (supplied by Finetex

[8] Schercemol DIS ® supplied by Scher Chemicals Inc.
[9] Supplied by Westwood Chemical Co.
[10] Westchlor DM200 ® supplied by Westwood Chemical Co.

| COMPONENT | X | XI | XII | XIII | XIV | XV | XVI | XVII | XVIII | XIX |
|---|---|---|---|---|---|---|---|---|---|---|
| N-Lauroyl-L-glutamic acid di-n-butyl amide[1] | 2 | 2 | 2 | 2 | 2 | 2 | 2 | 2 | 2 | 2 |
| 12-hydroxystearic acid | 6 | 6 | 6 | 6 | 6 | 6 | 6 | 6 | 6 | 6 |
| Cyclomethicone D-4[2] | q.s. | | q.s. | | q.s. | q.s. | q.s. | q.s. | | |
| Cyclomethicone D-5[3] | | q.s. | | q.s. | | | | | q.s. | q.s. |
| PPG-3-myristyl ether | | | | | | 12 | | | | |
| PPG-5-butyl ether | | | | | | | 10.5 | | | |
| PPG-10-cetyl ether | | | | | | | | 12.5 | | |
| Isocetyl alcohol | 7 | 8 | 13 | | | | | | | |
| Isostearyl alcohol | | | | 13 | | | | | | |
| Octyldodecanol | | | | | 8.5 | | | | 14 | 14 |
| Polydecene[4] | | | 26 | | | | | | | |
| Citric Acid | 4 | 1 | 10 | 0.1 | 2 | 5 | 0.2 | 0.5 | 0.01 | 0.05 |
| Ceteareth-20 ® | | | | | | | | | 2.5 | 2.5 |
| Dipropyleneglycol | | | | | | | | | | 0.25 |
| C20-40 alcohols[5] | | | | | | | | | 0.5 | 0.5 |
| C40-60 alcohols[6] | 0.5 | 0.5 | 0.5 | 0.5 | 0.5 | 0.5 | 0.5 | 0.5 | | |
| Aluminum Zirconium Trichlorhydrex Gly ®[7] | 26 | 26 | 26 | 26 | 26 | 26 | 26 | 26 | 26 | 26 |

[1] GP-1 ® supplied by Ajinomoto, Inc.
[2] Dow Corning 245 ® Fluid-cyclic polydimethylsiloxane
[3] Dow Corning 244 ® Fluid-cyclic polydimethylsiloxane
[4] Ethylflo 364 ® supplied by Ethyl Corp.
[5] Unilin 425 ® supplied by Petrolite
[6] Unilin 700 ® supplied by Petrolite
[7] Supplied by Westwood Chemical Co.

| COMPONENT | XX | XXI | XXII | XXIII | XXIV | XXV | XXVI |
|---|---|---|---|---|---|---|---|
| N-Stearyl-L-glutamic acid-di-n-hexyl amide[1] | 2 | 2 | | | | | |
| N-Lauroyl-L-glutamic acid-di-n-octyl amide[1] | | | 2 | 2 | | | |
| N-Lauroyl-L-glutamic acid-di-n-decyl amide[1] | | | | | 2 | | |
| N-Stearyl-L-glutamic acid-di-n-decyl amide[1] | | | | | | 2 | |
| N-Lauroyl-L-glutamic acid-di-n-stearyl amide[1] | | | | | | | 2 |
| 12-hydroxystearic acid | | | 6 | 6 | 6 | 6 | 6 |
| Isopropyl amide of 12-hydroxystearic acid[1] | 6 | 6 | | | | | |
| Cyclomethicone D-5[2] | q.s. | q.s. | q.s. | q.s. | q.s. | q.s. | q.s. |
| Salicylic Acid | 0.01 | 1 | 10 | 5 | 0.2 | 0.5 | 3 |
| C12–15 Alcohols Benzoate[3] | 25 | | 25 | | 25 | 25 | 25 |
| Octyldodecanol | | 14 | | 14 | | | |
| Ceteareth-20 ® | | 2.5 | | 2.5 | | | |
| C40-60 alcohols[4] | 0.5 | 0.5 | 0.5 | 0.5 | 0.5 | 0.5 | 0.5 |
| Aluminum Zirconium Trichlorhydrex Gly ®[5] | 26 | 26 | 26 | 26 | 26 | 26 | 26 |

[1] Supplied by Starks Chemical Co.
[2] Dow Corning 245 ® Fluid-cyclic polydimethylsiloxane
[3] Finsolv TN ® supplied by Finetex
[4] Unilin 700 ® supplied by Petrolite
[5] Supplied by Westwood Chemical Co.

Although particular embodiments of the subject invention have been described, it will be obvious to those skilled in the art that various changes and modifications of the subject invention may be made without departing from the spirit and scope of the invention. The appended claims are intended to cover all such modifications that are within the scope of the invention.

What is claimed is:

1. Antiperspirant gel composition comprising:

a. an effective amount of an antiperspirant active b. an effective amount of a gelling agent comprising a primary gellant selected from the group consisting of 12-hydroxystearic acid, esters of 12-hydroxystearic acid, amides of 12-hydroxystearic acid corresponding to the formula:

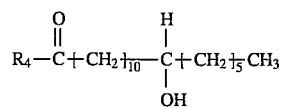

wherein $R_4$ is $OR_5$ or $NR_5R_6$; and $R_4$ and $R_5$ are, independently selected from the group consisting of hydrogen, alkyl moiety, aryl moiety having from 1 to about 26 carbon atoms and mixtures thereof; a secondary gellant selected from the group consisting of n-acyl amino acid amide derivatives corresponding to the formula:

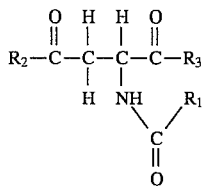

wherein $R_1$ is alkyl or aryl having from about 6 to about 22 carbon atoms; $R_2$ and $R_3$ are independently selected from the group consisting of alkyl ester, aryl ester, alkyl amide, aryl amide and mixtures thereof each having from about 1 to about 26 carbon atoms; and mixtures of said primary and secondary gellants;

c. an effective amount of a chelator selected from the group consisting of acetylacetone, ethylene diamine-N,N,N',N'-tetracetic acid, nitrilotriacetic acid, oxalate, citric acid, 1,2-diaminocyclohexane-N,N,N'N'-tetracetic acid, 4,5-dihydroxybenzene- 1,3-disulfonic acid, pyrocatechol-3,5-disulfonate, salicylic acid, 5-sulfosalicylic acid, xylenol orange, aurintricarboxylic acid, 2,2'-pyridyl ethylene diamine, glycine, 8-hydroxyquinoline- 5-sulfonic acid, lactic acid, 1,10-phenanthroline, pyridine, pyridine- 2,6-dicarboxylic acid, 8-quinolinol, succinic acid, tartaric acid, thioglycolic acid, 1,1,1-trifluoro- 3,2'-thenolyacetone, and triethylene tetramine; and salts and mixtures thereof; and d. an effective amount of a liquid base material.

2. The composition of claim 1 wherein the gelling agent comprises a mixture of said primary gellant and said secondary gellant having a ratio of said primary gellant to said secondary gellant from about 1:2 to about 20:1.

3. The composition of claim 2 wherein the composition is in the form of a gel stick.

4. The composition of claim 3 wherein the active is a complex of aluminum, zirconium and amino acids.

5. The composition of claim 1 wherein the chelator is selected from the group consisting of acetylacetone, ethylene diamine-N,N,N',N'-tetracetic acid, nitrilotriacetic acid, oxalate, citric acid, 1,2-diaminocyclohexane-N,N,N'N'-tetracetic acid, 4,5-dihydroxybenzene-1,3-disulfonic acid, pyrocatechol-3,5-disulfonate, salicylic acid, 5-sulfosalicylic acid, and xylenol orange; and salts and mixtures thereof.

6. The composition of claim 5 wherein the chelator is selected from the group consisting of acetylacetone, ethylene diamine-N,N,N',N'-tetracetic acid, nitrilotriacetic acid, and oxalate; and salts and mixtures thereof.

7. The composition of claim 6 wherein wherein the chelator is ethylene diamine-N,N,N',N'-tetracetic acid; or a salt thereof.

8. The composition of claim 7 wherein the chelator is disodium EDTA.

9. A process for manufacturing low-aqueous antiperspirant gel compositions comprising the steps of:

(a) pre-mixing a chelator with an active in a substantially water-free environment; and (b) adding a liquid base matrix, comprising a gelling agent and a liquid base material, to the product of step (a) in a subatantially water-free environment.

10. The process of claim 9 wherein:

(a) the pre-mixing step is conducted at a temperature ranging of about 200° F. for about 15 minutes to about one hour; and (b) and the chelator used is selected from the group consisting of acetylacetone, ethylene diamine-N,N,N',N'-tetracetic acid, nitrilotriacetic acid, oxalate, citric acid, 1,2-diaminocyclohexane-N,N,N'N' -tetracetic acid, 4,5-dihydroxybenzene-1,3-disulfonic acid, pyrocatechol-3,5-disulfonate, salicylic acid, 5-sulfosalicylic acid, xylenol orange, aurintricarboxylic acid, 2,2'-pyridyl ethylene diamine, glycine, 8-hydroxyquinoline-5-sulfonic acid, lactic acid, 1,10-phenanthroline, pyridine, pyridine-2,6-dicarboxylic acid, 8-quinolinol, succinic acid, tartaric acid, thioglycolic acid, 1,1,1-trifluoro-3,2'-thenolyacetone, and triethylene tetramine; and salts and mixtures thereof.

11. The process of claim 10 wherein the liquid base matrix is formed by heating the gelling agent and liquid base material in a vessel at a temperature of about 200° F., with stirring, until the mixture forms a homogeneous molten solution.

12. The process of claim 11 wherein the molten solution is added to the pre-mixed solution of step (a) and allowed to cool to a temperature ranging between about 135° F. and about 145° F. until thickening is observed.

13. The process of claim 12 wherein:

(a) the chelator used is ethylene diamine-N,N,N',N'-tetracetic acid, or a salt thereof;

(b) the active is a complex of aluminum, zirconium and amino acids;

(c) the gelling agent, comprises:

(i) a primary gellant selected from the group consisting of 12-hydroxystearic acid, esters of 12-hydroxystearic acid, amides of 12-hydroxystearic acid, and mixtures thereof; and (ii) a secondary gellant selected from the group consisting of n-acyl amino acid amide derivatives; and (d) the liquid base material comprises a volatile, non-polar oil and a non-volatile co-solvent which is more polar than the volatile, non-polar oil and soluble in the non-polar, volatile oil.

14. A substantially water free antiperspirant gel stick prepared according to the process of any of claims 9, 12, or 13.

\* \* \* \* \*

UNITED STATES PATENT AND TRADEMARK OFFICE
CERTIFICATE OF CORRECTION

PATENT NO. : 5,516,511
DATED : May 14, 1996
INVENTOR(S) : Curtis B. Motley and Barton J. Bradbury It is certified that error appears in the above-indentified patent and that said Letters Patent is hereby corrected as shown below:

Column 1, line 24, "Sagafin" should read --Sagarin--.
Column 5, line 53, "Sagafin" should read --Sagarin--.
Column 13, line 11 of EXAMPLE, "$C_{12}-C_{15}$" should read --$C_{12}-C_{15}$--.

Signed and Sealed this

Twenty-sixth Day of November 1996

Attest:

BRUCE LEHMAN

*Attesting Officer*    *Commissioner of Patents and Trademarks*